(12) United States Patent
Hedtke et al.

(10) Patent No.: US 10,190,968 B2
(45) Date of Patent: Jan. 29, 2019

(54) CORROSION RATE MEASUREMENT WITH MULTIVARIABLE SENSOR

(71) Applicant: Rosemount Inc., Shakopee, MN (US)

(72) Inventors: Robert C. Hedtke, Young America, MN (US); Charles R. Willcox, Chanhassen, MN (US)

(73) Assignee: ROSEMOUNT INC., Shakopee, MN (US)

( * ) Notice: Subject to any disclaimer, the term of this patent is extended or adjusted under 35 U.S.C. 154(b) by 64 days.

(21) Appl. No.: 14/751,298

(22) Filed: Jun. 26, 2015

(65) Prior Publication Data

US 2016/0377527 A1    Dec. 29, 2016

(51) Int. Cl.
  *G01N 17/04*    (2006.01)
  *G01N 17/00*    (2006.01)

(52) U.S. Cl.
  CPC .......... *G01N 17/04* (2013.01); *G01N 17/00* (2013.01)

(58) Field of Classification Search
  CPC .................. G01N 17/00; G01N 17/04
  See application file for complete search history.

(56) References Cited

U.S. PATENT DOCUMENTS

| | | | |
|---|---|---|---|
| 2,976,123 A | 3/1961 | Marsh et al. | 23/253 |
| 4,046,010 A | 9/1977 | Akeley | 73/406 |
| 4,468,613 A | 8/1984 | Slough et al. | 324/71.2 |
| 4,506,540 A | 3/1985 | Marsh | 73/29 |
| 4,935,195 A | 6/1990 | Palusamy et al. | |
| 5,061,846 A | 10/1991 | Gergely | 250/227.14 |
| 5,092,177 A | 3/1992 | Varacca | 73/708 |
| 5,127,433 A | 7/1992 | Argyle et al. | 137/559 |
| 5,253,674 A | 10/1993 | Argyle et al. | 137/559 |
| 5,301,001 A | 4/1994 | Murphy et al. | 356/35.5 |
| 5,447,073 A | 9/1995 | Kalinoski | 73/861.24 |
| 5,571,955 A | 11/1996 | Beavers et al. | 73/86 |
| 5,659,128 A | 8/1997 | Goldenberg | 73/53.01 |
| 5,683,594 A | 11/1997 | Hocker et al. | 216/33 |
| 5,731,523 A | 3/1998 | Cusumano et al. | 73/783 |
| 5,854,557 A | 12/1998 | Tiefnig | 324/700 |
| 5,948,971 A | 9/1999 | Brooker et al. | 73/86 |

(Continued)

FOREIGN PATENT DOCUMENTS

| CN | 1225733 | 8/1999 |
|---|---|---|
| CN | 1338043 | 2/2002 |

(Continued)

OTHER PUBLICATIONS

Notification of Transmittal of the International Search Report and the Written Opinion of the International Searching Authority from PCT/US2016/032020, dated Sep. 23, 2016.

(Continued)

*Primary Examiner* — Ryan Walsh (74) *Attorney, Agent, or Firm* — Westman, Champlin & Koehler, P.A.

(57) ABSTRACT

A corrosion measurement system includes a corrosion sensor having a corrosion sensor output related to corrosion due to exposure to a process fluid. A process variable sensor provides a process variable output related to a process variable of the process fluid. Measurement circuitry coupled to the corrosion sensor and the process variable sensor provides an output related to corrosion based upon the corrosion sensor output and the process variable output.

20 Claims, 6 Drawing Sheets

(56) References Cited

U.S. PATENT DOCUMENTS

| | | |
|---|---|---|
| 6,079,276 A | 6/2000 | Frick et al. ............... 73/718 |
| 6,280,603 B1 | 8/2001 | Jovancicevic ............. 205/775.5 |
| 6,294,133 B1 | 9/2001 | Sawada et al. ............ 422/82.01 |
| 6,341,185 B1 | 1/2002 | Elster et al. ............... 385/12 |
| 6,383,451 B1 | 5/2002 | Kim .......................... 327/71.1 |
| 6,426,796 B1 | 7/2002 | Pulliam et al. ............ 356/501 |
| 6,451,212 B2 | 9/2002 | Iseri et al. ................. 210/746 |
| 6,487,895 B2 | 12/2002 | Brooker et al. ............ 73/86 |
| 6,571,639 B1 | 6/2003 | May et al. .................. 73/800 |
| 6,671,055 B1 | 12/2003 | Wavering et al. .......... 356/478 |
| 6,931,937 B1 | 8/2005 | Tanaka et al. .............. 73/753 |
| 7,024,918 B2 | 4/2006 | Bell et al. .................. 73/37 |
| 7,034,553 B2 | 4/2006 | Gilboe |
| 7,131,335 B2 | 11/2006 | Textor ........................ 73/716 |
| 7,131,337 B2 | 11/2006 | Kato et al. ................. 73/754 |
| 7,290,450 B2 | 11/2007 | Brown et al. |
| 7,295,131 B2 | 11/2007 | Anderson et al. .......... 340/679 |
| 7,437,939 B1 | 10/2008 | Chakroborty et al. ..... 73/715 |
| 7,540,197 B2 | 6/2009 | Wavering et al. .......... 73/715 |
| 7,814,798 B2 | 10/2010 | Filippi et al. |
| 7,866,211 B2 | 1/2011 | Brown ........................ 73/579 |
| 2003/0006148 A1 | 1/2003 | Nielsen et al. ............ 205/775.5 |
| 2004/0055391 A1 | 3/2004 | Douglas et al. ............ 73/779 |
| 2005/0011278 A1 | 1/2005 | Brown ...................... 73/861.18 |
| 2005/0122121 A1 | 6/2005 | Gilboe ........................ 324/700 |
| 2005/0150279 A1 | 7/2005 | Taber et al. ................ 73/86 |
| 2005/0151546 A1 | 7/2005 | Taber .......................... 324/700 |
| 2006/0016265 A1 | 1/2006 | Kaneko et al. ............. 73/715 |
| 2006/0162431 A1 | 7/2006 | Harris ......................... 73/86 |
| 2006/0217902 A1 | 9/2006 | Bernard et al. ............. 702/47 |
| 2006/0260409 A1 | 11/2006 | Yane et al. .................. 73/716 |
| 2007/0019898 A1 | 1/2007 | Chimenti et al. ........... 385/12 |
| 2007/0074563 A1 | 4/2007 | Liu et al. .................... 73/54.24 |
| 2007/0120572 A1 | 5/2007 | Chen et al. ................. 324/700 |
| 2007/0199379 A1 | 8/2007 | Wolf et al. ................. 73/590 |
| 2007/0227252 A1 | 10/2007 | Leitko et al. ............... 73/717 |
| 2008/0141780 A1 | 6/2008 | Wavering et al. ........... 73/723 |
| 2008/0253058 A1 | 10/2008 | Chakraborty et al. ..... 361/283.4 |
| 2010/0064816 A1 | 3/2010 | Filippi et al. .............. 73/715 |
| 2015/0177033 A1* | 6/2015 | Clarke ...................... G01F 1/56 73/861.08 |
| 2015/0260633 A1 | 9/2015 | Hedtke et al. |
| 2015/0268111 A1 | 9/2015 | Hedtke |
| 2016/0091411 A1 | 3/2016 | Hedtke |
| 2016/0363525 A1* | 12/2016 | Friedersdorf .......... G01N 17/04 |

FOREIGN PATENT DOCUMENTS

| | | |
|---|---|---|
| CN | 1347496 | 5/2002 |
| CN | 1651883 | 8/2005 |
| CN | 1651886 | 8/2005 |
| CN | 1657893 | 8/2005 |
| CN | 1699191 | 11/2005 |
| CN | 1784589 | 6/2006 |
| CN | 1853098 | 10/2006 |
| CN | 201218797 | 4/2009 |
| CN | 102159928 | 8/2011 |
| CN | 204085538 | 1/2015 |
| EP | 0 240 236 | 10/1987 |
| EP | 0 971 214 | 1/2000 |
| EP | 0 984 252 | 3/2000 |
| EP | 2 124 034 | 11/2009 |
| JP | 53-065783 | 6/1978 |
| JP | 56-24510 | 3/1981 |
| JP | 61-177783 | 8/1986 |
| JP | H02-114149 | 4/1990 |
| JP | 3-183946 | 8/1991 |
| JP | 2000-131174 | 5/2000 |
| JP | 2000-171386 | 6/2000 |
| JP | 2000-266662 | 9/2000 |
| JP | 2001-4527 | 1/2001 |
| JP | 2002-277339 | 9/2002 |
| JP | 2003-014682 | 1/2003 |
| JP | 2006-258601 | 9/2006 |
| JP | 2007-021996 | 2/2007 |
| JP | 2007-531868 | 11/2007 |
| JP | 2008-261652 | 10/2008 |
| JP | 2009-250110 | 10/2009 |
| JP | 2010-523999 | 7/2010 |
| JP | 2012-503179 | 2/2012 |
| JP | 2012-093175 | 5/2012 |
| JP | 2012-237697 | 12/2012 |
| RU | 2225594 | 3/2004 |
| RU | 2286558 | 10/2006 |
| WO | WO 2002/16908 | 2/2002 |
| WO | WO 2006/065770 | 6/2006 |
| WO | WO 2009/016594 | 2/2009 |

OTHER PUBLICATIONS

Notification of Transmittal of the International Search Report and the Written Opinion of the International Searching Authority from PCT/US2015/020354, dated Jun. 2, 2015.
Office Action from Chinese Patent Application No. 201520148367. 8, dated May 19, 2015.
Notification of Transmittal of the International Search Report and the Written Opinion of the International Searching Authority from PCT/US2015/047905, dated Nov. 5, 2015.
Device Measurement and Maintenance, Issue 9, 1997, pp. 38-41.
Device Management and Maintenance, Issue 10, 1997, pp. 35-38.
Corrosion Test Methods and Monitoring Technology, Edition 1, May 2007, 9 pages.
1000 Examples of Water Disposal Anti-Corrosion and Invalidation Analysis, Sep. 2000, 4 pages.
Metal Corrosion Theory and Application, Dec. 1984, pp. 337-341.
Brochure entitled "CorrTran® MV Corrosion Monitoring Transmitter", by Pepperl+Fuchs, pp. 1-61, Mar. 2012.
Communication from European Patent Application No. 15714072. 4, dated Oct. 21, 2016.
Examination Report from Australian Patent Application No. 2015229218, dated Feb. 1, 2017.
Office Action from Chinese Patent Application No. 201510114343. 5, dated Feb. 28, 2017.
Communication from European Patent Application No. 15763727. 3, dated May 10, 2017.
Examination Report from Australian Patent Application No. 2015229218, dated Aug. 4, 2017.
Communication from European Patent Application No. 15714072. 4, dated Jun. 26, 2017.
Office Action from Canadian Patent Application No. 2,941,012, dated Jun. 6, 2017.
Office Action from Japanese Patent Application No. 2016-557291, dated Aug. 23, 2017.
Office Action from European Patent Application No. 15714072.4, dated Oct. 31, 2017.
Office Action from Chinese Patent Application No. 201510114343. 5, dated Oct. 31, 2017.
Examination Report for Australian Patent Application No. 2015324462, dated Oct. 10, 2017, 3 pages.
Office Action from European Patent Application No. 16736266.4, dated Feb. 2, 2018.
Office Action from Chinese Patent Application No. 201510931578. 3, dated Jun. 1, 2018.
Office Action from Russian Patent Application No. 2018102896, dated Jun. 26, 2018.
Office Action from Canadian Patent Application No. 2,988,562, dated Oct. 23, 2018.
Office Action from Japanese Patent Application No. 2017-567131, dated Dec. 4, 2018.

* cited by examiner

CORROSION RATE MEASUREMENT WITH MULTIVARIABLE SENSOR

BACKGROUND

The present invention relates to corrosion of components in various settings. More specifically, the present invention relates to monitoring such corrosion.

Corrosion is the gradual destruction of materials by chemical or other reaction with its environment. Corrosion degrades the useful properties of materials and structures including strength, appearance, and permeability to fluids. Many structural alloys corrode merely from exposure to moisture in air but the process can be strongly affected by exposure to certain substances. Corrosion can be concentrated locally to form a pit or crack, or it can extend across a wide area uniformly corroding the surface.

The field of corrosion measurement, control, and prevention is very broad. Corrosion measurement employs a variety of techniques to determine how corrosive the environment is and at what rate metal loss is being experienced. Some corrosion measurement techniques can be used on-line, constantly exposed to the process stream, while others provide off-line measurement, determined in a laboratory analysis. Some techniques give a direct measure of metal loss or corrosion rate while others are used to infer that a corrosive environment may exist.

The rate of corrosion dictates how long any process plant can be usefully and safely operated. The measurement of corrosion and the action to remedy high corrosion rates permits the most cost effective plant operation to be achieved while reducing the life-cycle costs associated with the operation.

The following list details common corrosion monitoring techniques which are used in industrial applications.
 Corrosion Coupons (weight loss measurements)
 Electrical Resistance (ER)
 Linear Polarization Resistance (LPR)
 Galvanic (ZRA) I Potential
 Hydrogen Penetration
 Microbial
 Sand/Erosion The weight loss technique is the best known and simplest corrosion monitoring technique. The method involves exposing a specimen of material (coupon) to a process environment for a given duration, then removing the specimen for analysis. The basic measurement which is determined from corrosion coupons is weight loss. Corrosion rate can be calculated by dividing the weight loss by material density, coupon surface area, and time of exposure. Coupon monitoring is most useful in environments where corrosion rates do not significantly change over long time periods. However, they can provide a useful correlation with other techniques.

ER probes can be thought of as "electronic" corrosion coupons. ER probes provide a basic measurement of metal loss and the value of metal loss can be measured at any time while the probe is in-situ. The ER technique measures the change in electrical resistance of a corroding metal element exposed to the process. The action of corrosion on the surface of the element produces a decrease in its cross-sectional area with a corresponding increase in its electrical resistance.

The LPR technique is based on electro-chemical theory. A small voltage is applied to an electrode in solution. The current needed to maintain a specific voltage shift (typically 10 mV) is directly related to the corrosion on the surface of the electrode in the solution. By measuring the current a corrosion rate can be derived. The advantage of the LPR technique is that the measurement of corrosion rate is made instantaneously whereas with coupons or ER some period of exposure is required to determine corrosion rate. The LPR technique can only be performed in clean aqueous electrolytic environments and will not work in gases.

Corrosion is an expense in many systems. The impact of corrosion includes lost production, system down time, system failures, as well as repair time and expense. There is an important need to prevent and monitor corrosion.

SUMMARY

A corrosion measurement system includes a corrosion sensor having a corrosion sensor output related to corrosion due to exposure to a process fluid. A process variable sensor provides a process variable output related to a process variable of the process fluid. Measurement circuitry coupled to the corrosion sensor and the process variable sensor provides an output related to corrosion based upon the corrosion sensor output and the process variable output.

This Summary and the Abstract are provided to introduce a selection of concepts in a simplified form that are further described below in the Detailed Description. The Summary and the Abstract are not intended to identify key features or essential features of the claimed subject matter, nor are they intended to be used as an aid in determining the scope of the claimed subject matter.

DETAILED DESCRIPTION OF ILLUSTRATIVE EMBODIMENTS

A system for measuring corrosion and an industrial process is provided which includes a corrosion sensor as well as an additional (or secondary) process variable sensor. Outputs from the corrosion sensor and the process variable sensor are used to provide additional information such as a corrosion rate determination with improved accuracy, predictive corrosion related information, compensation related information, performance related information or other information. The corrosion sensor may be in accordance with any appropriate technology. Similarly, the process variable sensor may sense any process variable including, but not limited to, pressure, temperature, flow, level, turbidity, pH, conductivity, etc.

Many operators currently inspect for corrosion during scheduled repair and maintenance at either fixed or unplanned intervals. New technologies are enabling monitoring of corrosion in real time using the plant control and automation system. This allows the assessment of corrosion in shorter time intervals with the ability to control and mitigate the rate of damage.

By integrating corrosion measurements into automation systems, corrosion monitoring is easier to implement, automate, and view with other process variables. This approach is more cost-effective than conventional stand-alone systems, requires less manual labor, provides a greater degree of integration with systems to record, control, and optimize.

It is desirable for plant operators to increase efficiency and productivity by even small amounts. However, corrosion costs are one of the few areas in plant operations where large improvements are possible along with associated cost-reduction. Corrosion measurement can be considered a primary variable that is subject to control and optimization in the process.

Corrosion measurement is challenging due to a number of factors including the numerous types of corrosion, various corrosive agents, a variety of vessel materials, unique chemical effects and dependence of corrosion on variables such as temperature and pressure. A multivariable corrosion sensor is provided which includes not only a sensor to sense corrosion directly, but also a secondary process variable sensor.

Figure 1:
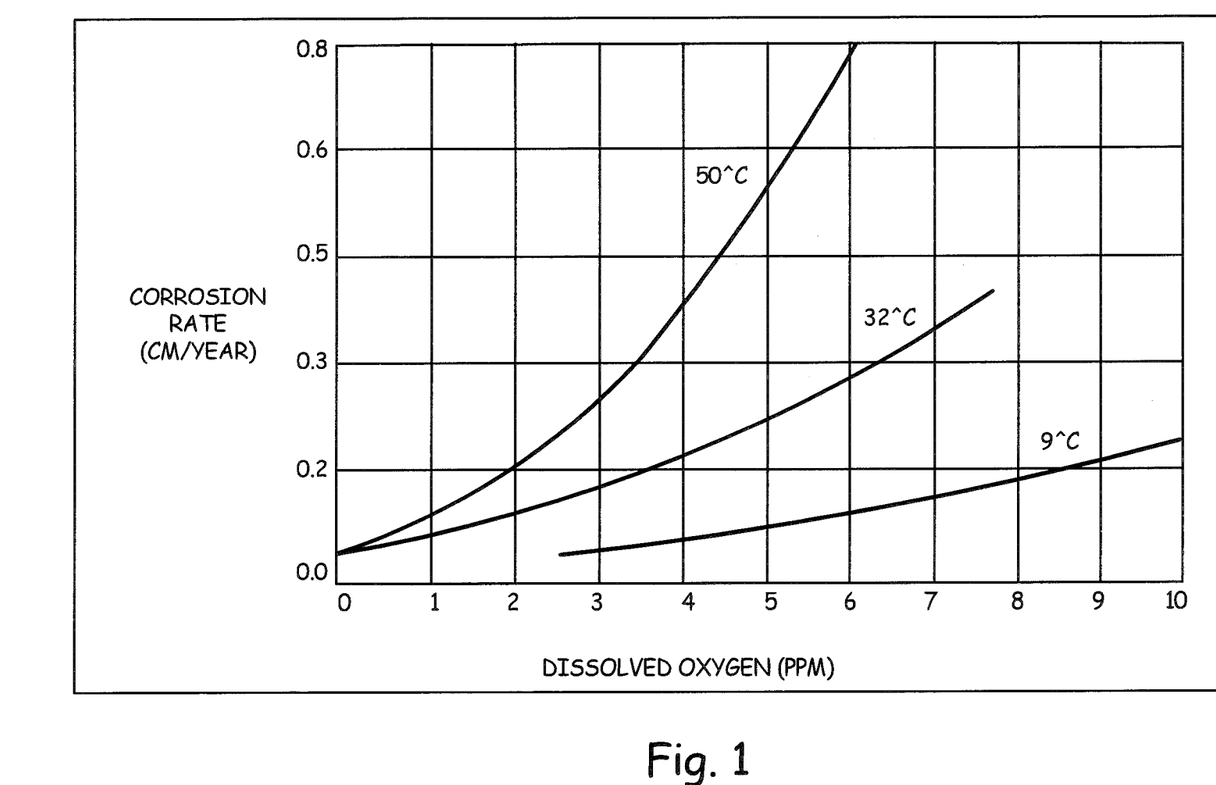
FIG. 1 is a graph illustrating relationships between corrosion rate and temperature.

Corrosion rate may be influenced by a number of factors such as temperature, pressure and flow rate. For example, FIG. 1 is a graph showing corrosion as a function of dissolved oxygen concentration at various temperatures. In addition to temperature changes arising within the process, the corrosion process itself can be exothermic causing a temperature rise that may need to be accounted for in order to accurately determine a corrosion rate.

Figure 2A:
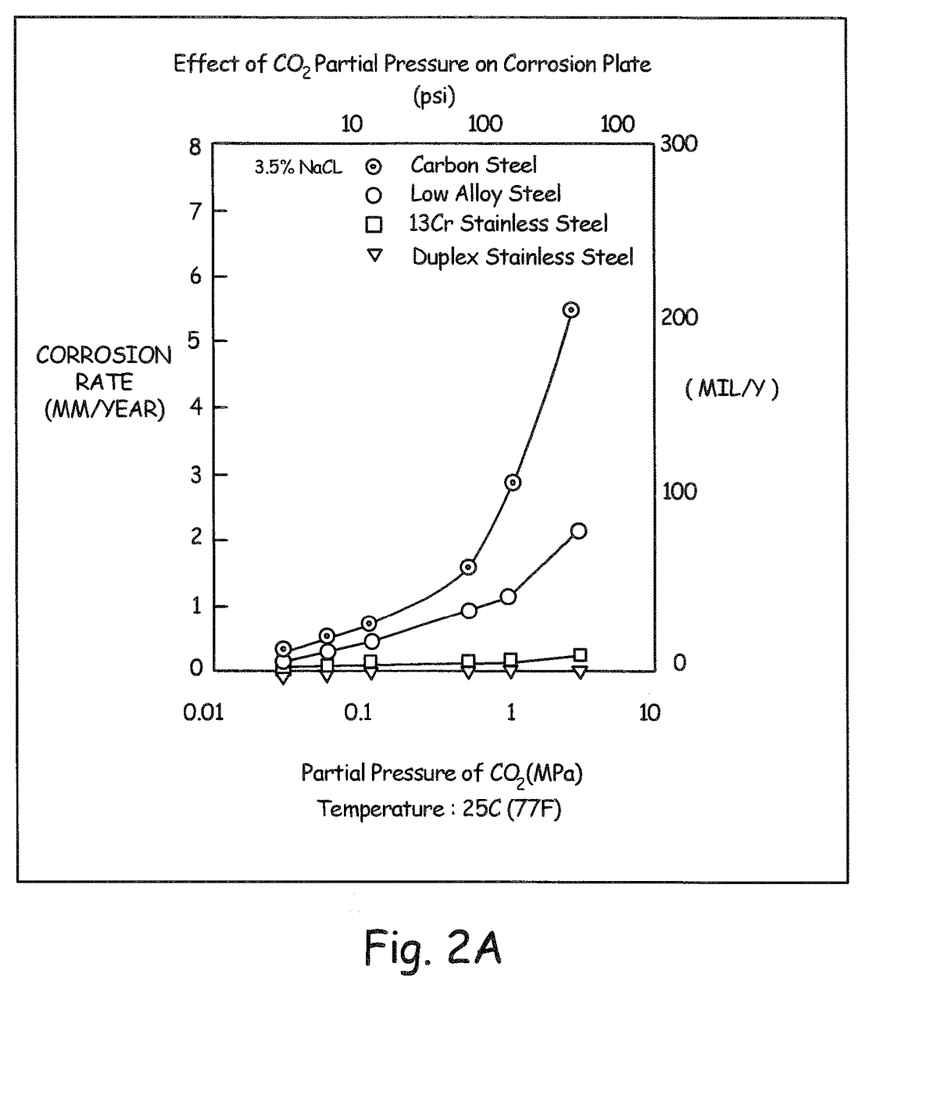
FIGS. 2A and 2B are graphs illustrating relationships between pressure and corrosion rate.
Figure 2B:
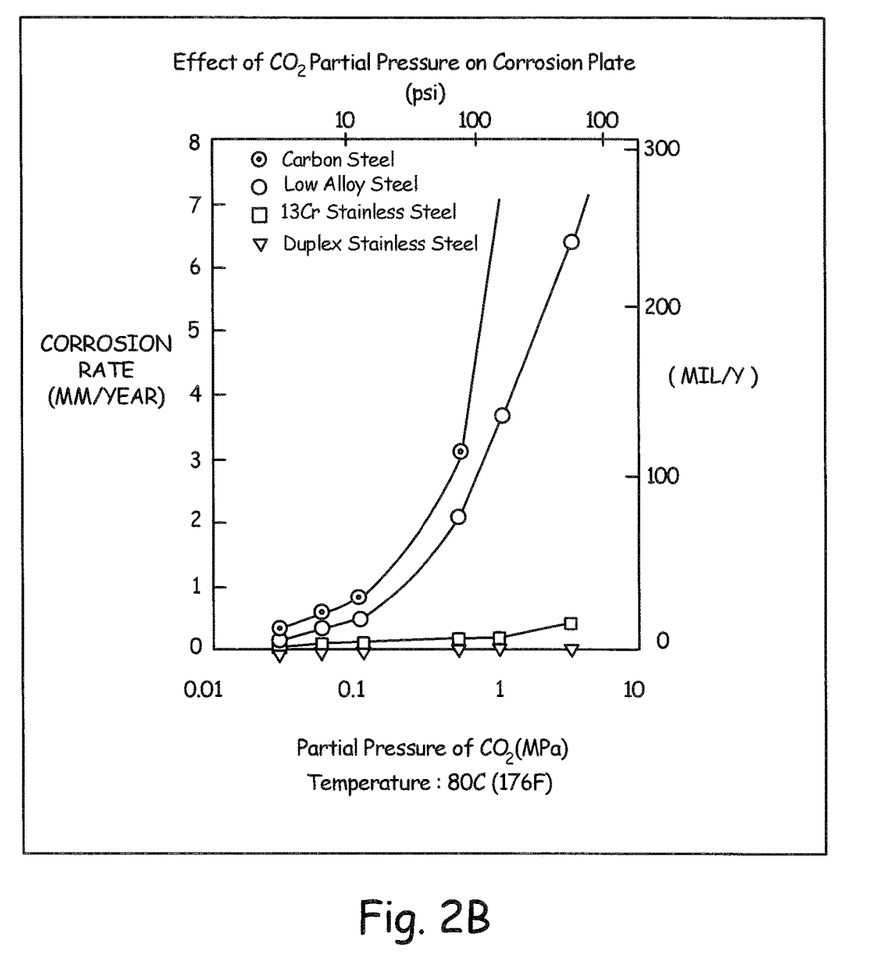

Similarly, in many instances, corrosion rate increases at increasing pressure. This may be due to a number of sources such as significant corrosion agents, for example $CO_2$, $H_2S$ and $O_2$ being more soluble in water at higher pressure. FIGS. 2A and 2B are graphs of corrosion rate versus pressure at two different temperatures.

Figure 3:
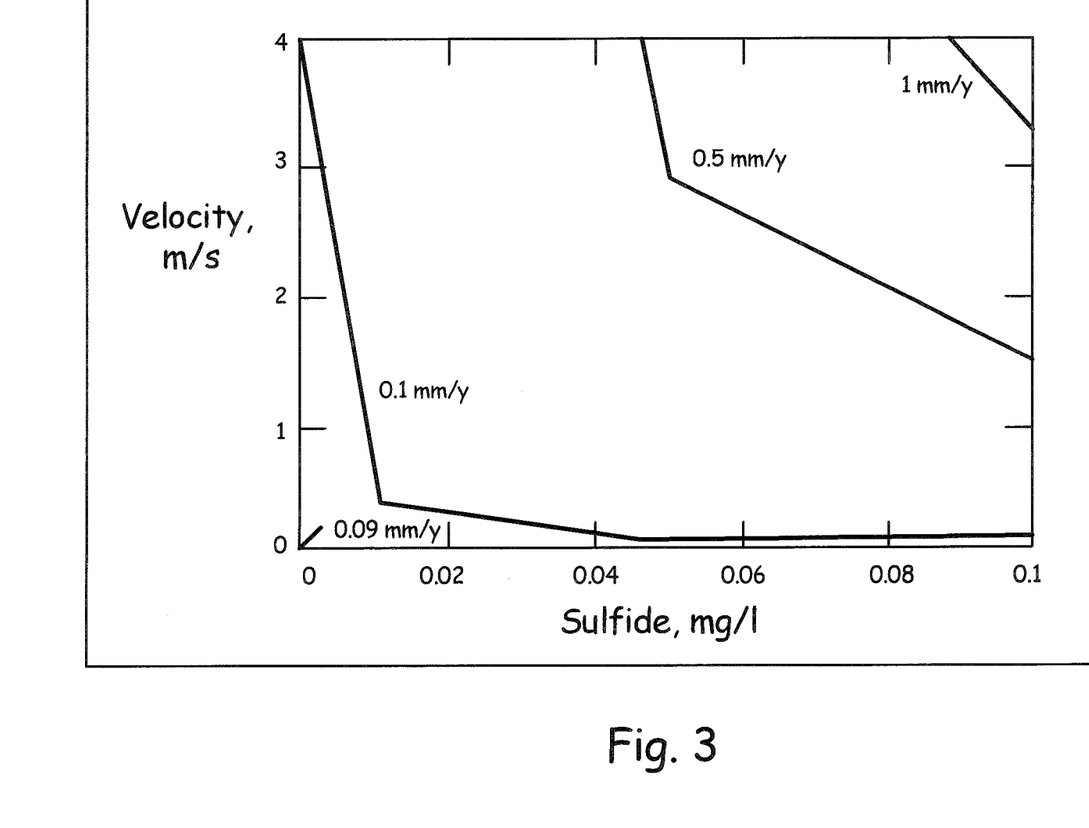
FIG. 3 is a graph illustrating relationships between flow and corrosion rate.

Similar to pressure and temperature, flow rate may also cause an increase in the rate of corrosion. The increased corrosion rate may be due to increased erosion from the presence of solid particulates such as sand in a process fluid. Increasing flow will also increase chemical corrosion rates through different mechanisms such as the stripping away corrosion inhibiting films or replenishing of corrosive agents such as dissolved oxygen. FIG. 3 is a graph of flow velocity versus various concentrations of sulfide showing the increasing corrosion rate with increasing flow velocity.

As previously discussed, it would be desirable to provide improved corrosion measurement information. Such improvements include ease of use, improved performance, obtaining multiple process variable measurements, providing predictive analytics and customizable application information specific to unique process conditions.

Figure 4:
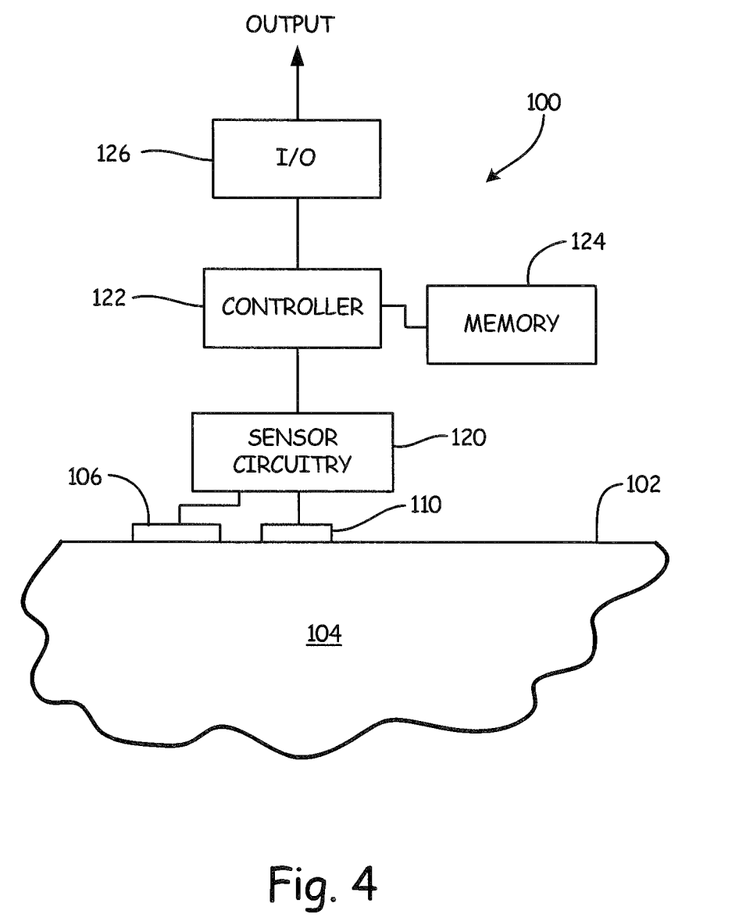
FIG. 4 is a simplified block diagram of a corrosion measurement system for measuring corrosion based upon an output from a corrosion sensor and a secondary process variable sensor.

FIG. 4 is a simplified block diagram showing a multivariable corrosion rate measurement system 100 coupled to a process vessel 102 in accordance with one example embodiment. Process vessel 102 carries a corrosive process fluid 104. System 100 includes a process variable sensor 110 which is configured to sense a process variable of the process fluid 104. A corrosion sensor 106 is arranged to provide an output which is related to corrosion. The corrosion sensor 106 operates in accordance with any appropriate technology including those specifically discussed herein as well as others. The corrosion sensor 106 may be directly coupled to the process fluid 104 or can remotely monitor the fluid 104. The corrosion sensor 106 may also be implemented for non-invasive corrosion measurement. Corrosion sensor 106 is coupled to sensor circuitry 120 which is configured to measure an output or characteristic of the corrosion sensor 106. Example characteristics include resistance, capacitance, voltage, etc. Process variable sensor 110 also provides an output related to a process variable to the sensor circuitry 120. As discussed above, the particular process variable may be any process variable of the industrial process.

A controller 122 couples to the sensor circuitry 120 and is configured to operate in accordance with instructions stored in a memory 124. However, the controller can be more basic circuit such as a comparator, or may comprise more complex circuitry such as a microprocessor. Based upon the output from the sensor circuitry 120, the controller can communicate over I/O circuitry 126 and provide an output related to the corrosion rate as sensed by the sensor 106. Sensor circuitry 120, controller 122 and memory 124 provide one example configuration of measurement circuitry for use in determining corrosion.

The system 100 illustrated in FIG. 4 provides a multivariable measurement to corrosion sensor 106. The process variable sensor 110 may be a pressure, temperature, level, flow, or other sensor including analytical sensor such as pH, oxygen, conductivity, etc. Any number of additional process variable sensors may also be implemented. The system 100 may be implemented in a standard configuration such as that used with existing process variable transmitters as discussed below.

Figure 5:
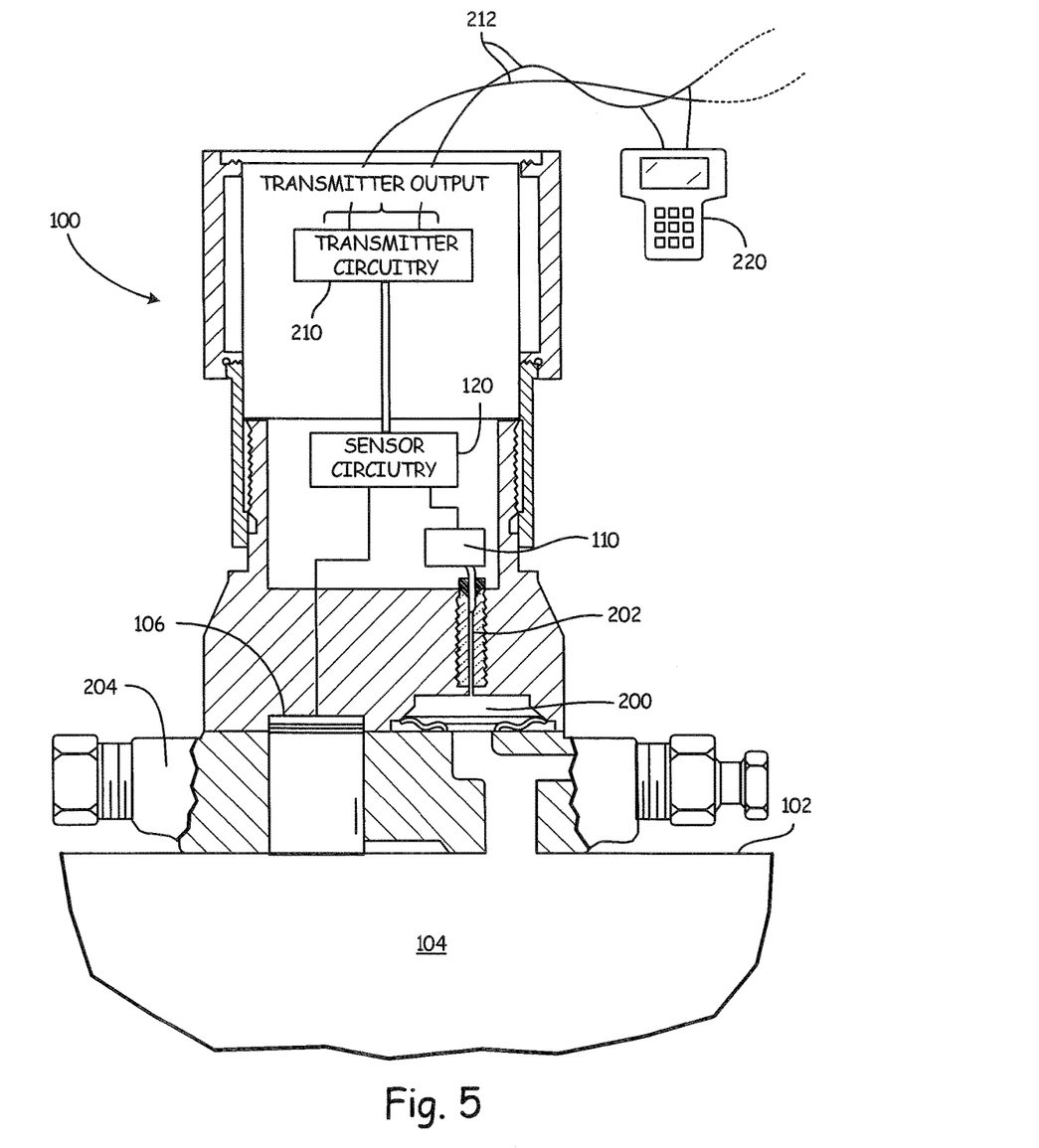
FIG. 5 is a side cross-sectional view of the corrosion measurement system of FIG. 4 implemented in a process variable transmitter.

FIG. 5 is a cross-sectional view of an example configuration in which the corrosion measurement system 100 is implemented in a traditional process variable transmitter configuration. The configuration illustrated in FIG. 5 allows measurements of multiple process variable from a single process penetration. In the example of FIG. 5, process variable sensor 110 is illustrated as being implemented as a pressure sensor. As illustrated in FIG. 5, corrosion sensor 106 is arranged to measure corrosion of material due to exposure to process fluid 104. The pressure sensor 110 is isolated from the process fluid 104 by an isolation diaphragm 200. Isolation diaphragm 200 deflects in response to a pressure applied from process fluid 104 and transfers this pressure to pressure sensor 110 using an isolation fill fluid carried in a capillary system 202. The transmitter 100 is shown coupled to process piping 102 using a flange 204. However, any appropriate coupling technique may be implemented.

Sensor circuitry 120 is illustrated as coupling to transmitter circuitry 210 which provides an output. The output may be over a wired connection such as process control loop 212. Wireless control loops may also be implemented. Examples of wired communication techniques include a 4 to 20 mA signal as well as such an analog signal with additional digital information modulated thereon such as in accordance with the HART® Communication Protocol. Fully digital communication techniques may also be implemented. Example wireless communication techniques include the Wireless HART® communication protocol in accordance with the IEC 62591 Standard. The corrosion measurement system 100 may be powered with power received over the process control loop 212 or through some other source including an internal power source such as a battery.

Memory 124 illustrated in FIG. 4 may be used to store configuration information including constants related to the process fluid, vessel material, corrosive agents, compensation information such as a polynomial coefficients, lookup tables, etc. This information may be stored in memory from a remote location such as a process control room, or using a hand held calibrator 220 illustrated in FIG. 5. Such information may also be configured during manufacture or installation of the system 100. During operation, the controller 122 determines corrosion rate, total corrosion, predictive corrosion, etc. as desired and responsively provides an output over loop 212. Information such as look up tables can be stored in memory 124 and used to store configuration information such as a correlation between various vessel materials and their corrosion rates due to exposure to a particular corrosive agent at a particular temperature, pressure, flow rate, etc.

Corrosion typically occurs at a relatively slow rate. Therefore, corrosion rate measurements do not need frequent updates and the system 100 is well suited for a wireless environment. More accurate corrosion rate determination can be obtained using the additional process variable. The information can be used to verify that corrosion rates are within design limits for a particular configuration or process. The information can be used to predict corrosion rates and vessel life based upon constants stored in the memory as well as measurement variables. The system 100 can provide actionable information rather than just a raw output. For example, an operator may be alerted that a particular component in the process should be replaced or repaired due to corrosion. The system 100 may be implemented in a single housing such as illustrated in FIG. 5. However, in such a configuration it is difficult to replace or repair the corrosion sensor. In another configuration, the system 100 may receive a process variable from a remote location such as a remote sensor. Either or both of the corrosion sensor and additional process variable sensor may be implemented remotely. In another example configuration, the information from the corrosion sensor and the additional process variable are communicated to a remote location such as a communication gateway. The actual corrosion rate determination is made in the communication gateway or at the remote location. Such a configuration is useful when used with a non-intrusive corrosion sensor probe such as an ultrasonic system or the like.

System 100 provides an output related to corrosion. The determination of this corrosion related output may be through any appropriate technique including the use of a look up table stored in memory 124, curve fitting techniques using polynomial coefficients stored in memory 124, a rules based analysis, a fuzzy logic implementation, etc. The corrosion sensor may be any type of corrosion sensor including those discussed herein. Example corrosion measurement system are illustrated in U.S. Ser. No. 14/656,850, filed Mar. 13, 2015, entitled CORROSION RATE MEASUREMENT and U.S. Ser. No. 14/501,755, filed Sep. 30, 2014, entitled CORROSION RATE MEASUREMENT USING SACRIFICIAL PROBE, which are incorporated herein by reference in their entirety.

In one configuration, the process variable sensor 110 comprises a temperature sensor which is positioned proximate the corrosion sensor 106. This allows the temperature sensor to detect exothermic temperature changes due to corrosion of the corrosion sensor 106. Other sources of corrosion may also cause exothermic temperature changes which are measured by such a temperature sensor. Corrosion measurements can be used to compensate for exothermic temperature changes which may be sensed by a temperature sensor. Similarly, sensed temperature may be used to compensate a corrosion measurement.

Remote programming techniques can be used to store information in the system 100. This may be through a hand held calibrator or a communication from a centralized location such as a process control room. Inputs can be received by the device related to constants such as process fluid, vessel material, etc. Other information related to corrosion dependencies such as corrosion rate versus a process variable may also be received and stored. Predictive analysis can be implemented based upon known variables as well as measured process variables and measured corrosion rate. A relationship between an output from a corrosion sensor and an output from another process variable sensor can be used for diagnostics purposes including identification of a failure in a device or some event which may have occurred in the process.

In some configurations, the controller 122 includes a clock. Information from the clock can be used to time stamp the measured corrosion rate or the additional process variable for example, for use in determination of a histogram as well as for determination of rate of change. The information, including time information, may also be logged for subsequent analysis.

In one example configuration, the system is self-learning and monitors a relationship between measured corrosion and the measured secondary process variable. Examples of self-learning features include providing an alarm, sample rate determination, etc. In one example configuration, the sampling rate of at least one of the corrosion sensor and/or process variable sensor may be changed based upon an output from the other sensor. For example, if a flow rate measurement increases substantially, the sampling rate of the output from the corrosion sensor can be increased accordingly. This allows the system to operate using reduced power during periods of reduced corrosion.

Although the present invention has been described with reference to preferred embodiments, workers skilled in the art will recognize that changes may be made in form and detail without departing from the spirit and scope of the invention. As used herein, the additional process variable sensor measures an additional (or secondary) process variable in addition to the corrosion sensor. The system can be used to measure corrosion rate, predicted corrosion rate, expected life or health of a process component, as well as perform diagnostics.

What is claimed is:

1. A corrosion measurement system, comprising:
   a corrosion sensor having a corrosion sensor output related to corrosion due to exposure to a process fluid;
   a process variable sensor having a process variable output related to a process variable of the process fluid wherein the process variable changes a rate at which components exposed to the process fluid corrode; and
   measurement circuitry coupled to the corrosion sensor and the process variable sensor having an output related to corrosion of components exposed to the process fluid based upon the corrosion sensor output and the process variable output wherein the measurement circuitry identifies periods of reduced corrosion rate and uses reduced power during the periods of reduced corrosion rate.

2. The corrosion measurement system of claim 1 wherein the process variable sensor comprises a pressure sensor.

3. The corrosion measurement system of claim 1 wherein the process variable sensor comprises a temperature sensor.

4. The corrosion measurement system of claim 1 wherein the process variable sensor comprises a flow sensor.

5. The corrosion measurement system of claim 1 wherein the corrosion sensor and process variable sensor are carried in a single housing.

6. The corrosion measurement system of claim 1 wherein at least one of the corrosion sensor and process variable sensor is located remotely.

7. The corrosion measurement system of claim 1 wherein the output related to corrosion further comprises an output that is indicative of corrosion rate.

8. The corrosion measurement system of claim 1 wherein the output related to corrosion further comprises an output that is indicative of remaining life of a process component.

9. The corrosion measurement system of claim 1 wherein the output related to corrosion further comprises diagnostic information.

10. The corrosion measurement system of claim 1 including a memory configured to store information related to the process fluid.

11. The corrosion measurement system of claim 1 including a memory configured to store information related to a process vessel.

12. The corrosion measurement system of claim 1 including a memory configured to store information related to a correlation between the corrosion output and the process variable output and corrosion of a process component.

13. The corrosion measurement system of claim 12 wherein the correlation is based upon a look up table.

14. The corrosion measurement system of claim 12 wherein the correlation is based upon a curve fit.

15. The corrosion measurement system of claim 1 wherein the output related to corrosion further comprises an actionable output.

16. The corrosion measurement system of claim 15 wherein the actionable output comprises an output instructing an operator to replace a component.

17. The corrosion measurement system of claim 1 including a clock.

18. The corrosion measurement system of claim 17 wherein the output related to corrosion includes time related information from the clock.

19. The corrosion measurement system of claim 1 wherein the output related to corrosion comprises a wireless output.

20. The corrosion measurement system of claim 1 wherein a sampling rate of the corrosion sensor output is changed as a function of the process variable output.

* * * * *